United States Patent [19]

Takanashi

[11] Patent Number: 4,687,474
[45] Date of Patent: Aug. 18, 1987

[54] JUNCTION FOR MEDICAL INSTRUMENTS

[75] Inventor: Nobuyasu Takanashi, Fujinomiya, Japan

[73] Assignee: Terumo Kabushiki Kaisha, Tokyo, Japan

[21] Appl. No.: 815,176

[22] Filed: Dec. 20, 1985

Related U.S. Application Data

[63] Continuation of Ser. No. 742,653, Jun. 10, 1985, abandoned, which is a continuation of Ser. No. 426,204, Sep. 28, 1982, abandoned.

[30] Foreign Application Priority Data

May 28, 1982 [JP] Japan ................................. 57-89863

[51] Int. Cl.4 ........................................... A61M 5/185
[52] U.S. Cl. .................................. 604/257; 604/258; 604/262; 604/409
[58] Field of Search ............... 604/257, 258, 262, 408, 604/411, 6, 86, 414, 415, 403, 905; 285/423, DIG. 10, DIG. 16, DIG. 24, DIG. 20; 156/296, 333

[56] References Cited

U.S. PATENT DOCUMENTS

| | | | |
|---|---|---|---|
| 2,327,128 | 8/1943 | Renfrew et al. | 285/DIG. 24 |
| 2,619,086 | 11/1952 | Wylde | 604/257 |
| 2,949,712 | 8/1960 | Bieberdorf et al. | 604/262 X |
| 4,007,738 | 2/1977 | Yoshino | 604/262 X |
| 4,256,333 | 3/1981 | Jones | 285/423 |
| 4,327,726 | 5/1982 | Kwong et al. | 604/262 |

FOREIGN PATENT DOCUMENTS 715953 9/1954 United Kingdom ................ 156/333

OTHER PUBLICATIONS

Polymer Processing; Schildknecht (editor); vol. X; 1956 Interscience Publishers; New York; pp. 551-557, 563-567.

"Vinyl and Allied Polymers"; vol. 2; Matthews et al.; 1972; ILIFFE Books; pp. 76-83.

Primary Examiner—Richard J. Apley
Assistant Examiner—Alan W. Cannon
Attorney, Agent, or Firm—Frishauf, Holtz, Goodman & Woodward

[57] ABSTRACT

Junction for a medical instrument, which permits the opposed ends for union in two tubular members of a medical instrument made of vinyl chloride polymer to adhere fast to each other with a combination of vinyl chloride polymer paste resin and a plasticizer.

22 Claims, 4 Drawing Figures

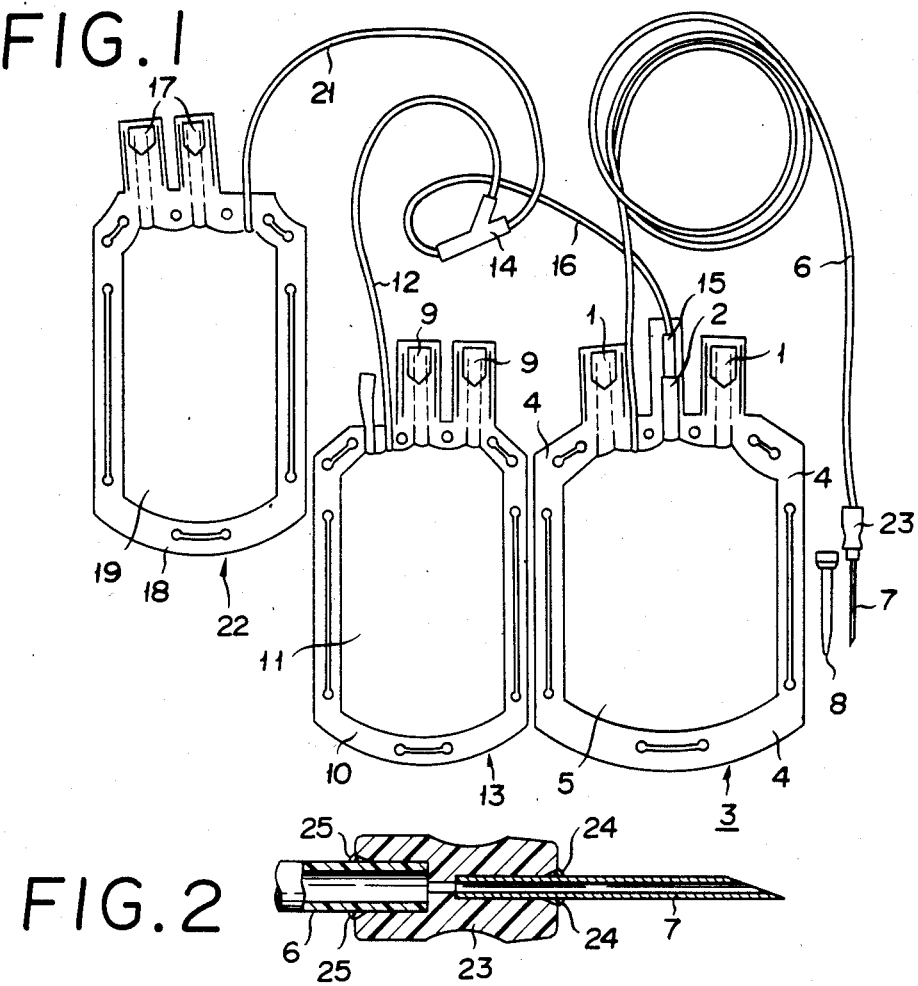
FIG.1
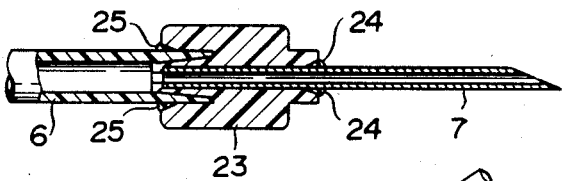
FIG.2
FIG.3
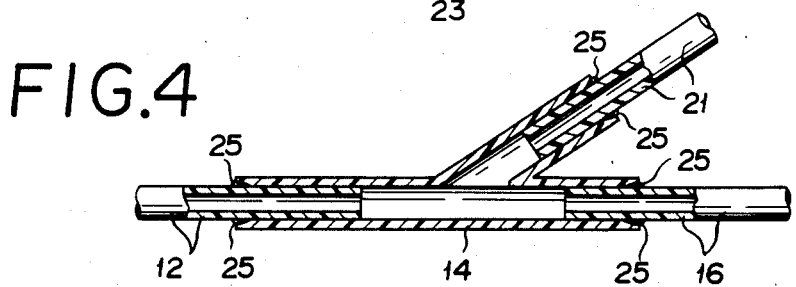
FIG.4

JUNCTION FOR MEDICAL INSTRUMENTS

This application is a continuation of application Ser. No. 742,653, filed June 10, 1985, now abandoned, which is a continuation of Ser. No. 426,204 filed Sept. 28, 1982, now abandoned.

BACKGROUND OF THE INVENTION

1. Field of the Invention

This invention relates to junction for medical instruments, and more particular to a junction for tubular members in medical instruments made of polyvinyl chloride such as blood bags and transfusion solution bags.

2. Description of the Prior Art

Heretofore, medical instruments such as blood bags and transfusion bags have been mostly made of polyvinyl chloride by reason of high fabricability, physiological safety, high transparency, low price and the like. They are provided at various portions thereof with tubular members. Proper junction of these tubular members is necessary for such instruments. In the case of a blood bag of one type, for example, one blood collection bag has connected thereto a blood collection tube which is connected to a hub having a blood collection needle fastened to the leading end thereof. A blood bag of another type comprises at least one auxiliary bag besides the aforementioned blood collection bag fitted with a blood collection needle, a hub and a blood collection tube. The auxiliary bags themselves as well as the auxiliary bag and the blood collection bag are interconnected through connection tubes with the aid of a manifold.

The joining members used for the blood collection tube, between the blood collection tube and the manifold, and between the connection tubes and the manifold, for example, are relatively thin, long tubes. Since they are too thin to admit a core wire, their union by high-frequency heating has so far been impractical. The union of two such tubular members, therefore, has heretofore been accomplished by applying a solvent such as, for example, tetrahydrofuran (THF) which is capable of dissolving vinyl chloride polymers, to the ends of the tubular members to be joined thereby partially dissolving the ends, and thereafter fitting one of the dissolved ends into the other, for example. Another method of effecting the union of such tubular members is carried out by inserting one of the ends of the tubular members not yet treated with the solvent into the other, applying the aforementioned organic solvent to a fine gap between the joined ends thereby allowing the applied solvent to seep through the annular interface of the joined ends by capillary action and induce partial dissolution of the joined ends and thereafter causing the partially dissolved ends to fuse with each other and resolidify.

The method which employs an organic solvent has the disadvantage that sufficient seepage of the organic solvent through the interface and, consequently, thorough union of the joined ends of the tubular members is not obtained when the aforementioned gap is too small. If excess solvent is used and the gap is too large, the solvent can flow out of the joined ends. In the case of a blood bag already containing an anticoagulant or a transfusion bag containing a medicinal solution for transfusion, for example, the excess solvent may find its way into the solution in the bag. The use of the organic solvent has the disadvantage that the joined ends tend to undergo blushing or gradual degradation and the organic solvent itself, because of its high volatility, tends to jeopardize the manufacturing facility and inflict cracks on molded articles of polyvinyl chloride.

SUMMARY OF THE INVENTION

It is, therefore, an object of this invention to provide a new junction for medical instruments. Another object of this invention is to provide a highly stable junction for tubular members in medical instruments made of vinyl chloride polymer, which permits the union of tubular members to be effected with high efficiency and without using organic solvents which can mingle with the medicinal solutions contained in the instruments.

The objects described above are attained by a junction for medical instruments, which permits the union of two tubular members of a medical instrument made of vinyl chloride polymer to adhere fast to each other, the junction is made possible by a vinyl chloride polymer paste resin incorporating therein a plasticizer.

BRIEF DESCRIPTION OF THE DRAWINGS

FIGS. 2-4 are enlarged sectional diagrams each illustrating a junction of tubular members according to the present invention.

DESCRIPTION OF THE PREFERRED EMBODIMENTS

Figure 1:
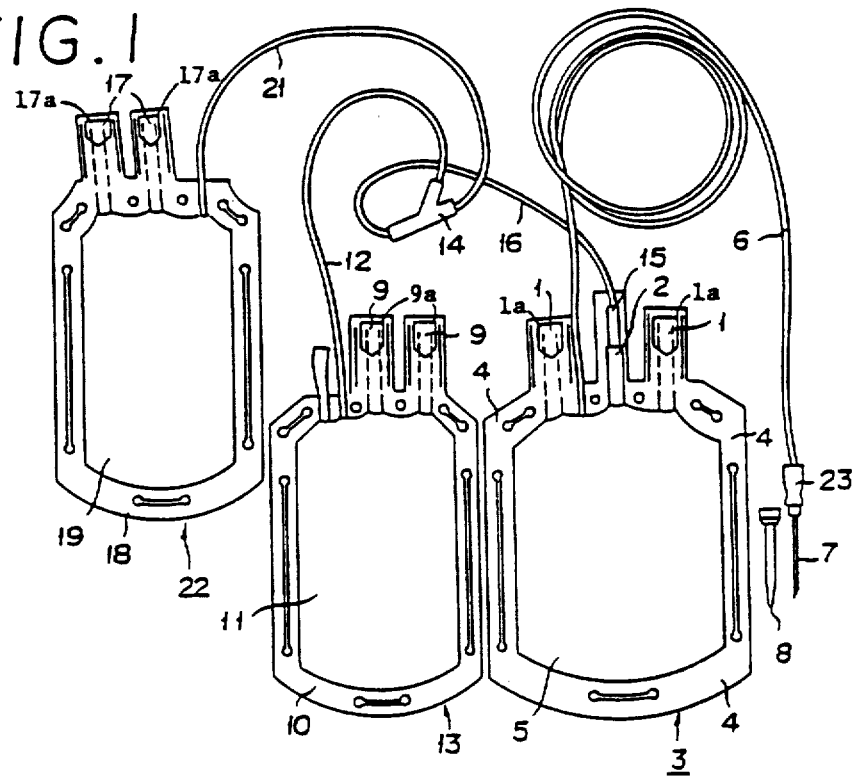
FIG. 1 is a front view illustrating a typical medical instrument employing the junction for tubular members according to the present invention.

The vinyl chloride polymer paste resin incorporating a plasticizer which is to be used in this invention is a substance obtained by uniformly dispersing and suspending in a plasticizer a vinyl chloride polymer finely divided to a particle diameter in the range of 0.02 to 20 $\mu$m, preferably 0.1 to 10 $\mu$m. Examples of the vinyl chloride polymer thus used in a finely divided state are a homopolymer of vinyl chloride and copolymers of vinyl chloride with such comonomers as vinylidene chloride, vinyl acetate, vinyl alcohol and vinyl bromide. In the case of such a copolymer, the amount of the comonomer to be copolymerized with vinyl chloride is not more than 50 mol%, preferably not more than 30 mol%, most preferably from 3 to 7 mol%. The average degree of polymerization of the homopolymer or copolymer is 900 to 1200, preferably from 960 to 1130.

The paste resin is formed by dispersing and suspending the finely divided vinyl chloride polymer in a plasticizer. The solids content of the paste resin is from 25 to 50% by weight, preferably from 30 to 50% by weight. Examples of the plasticizer to be used for suspending therein the vinyl chloride polymer are phthalic esters such as di-2-ethylhexyl phthalate, di-n-octyl phthalate, diisooctyl phthalate, diheptyl phthalate, didecyl phthalate, diisodecyl phthalate, octyldecyl phthalate and butylbenzyl phthalate; trimellitic esters such as tributyl trimellitate and trioctyl trimellitate; aliphatic polybasic acid esters such as dioctyl adipate, dioctyl azelate and dioctyl sebacate; phosphoric esters such as tricresyl phosphate, trixylenyl phosphate, monooctyldiphenyl phosphate, monobutyl-dixylenyl phosphate and trioctyl phosphate; citric esters such as tributylacetyl citrate, trioctylacetyl citrate; and tributyl citrate; and butylphthalylbutyl glycolate.

The adhesive agent to be used in the present invention is prepared by further adding to the paste resin described above 50 to 350 parts by weight, more desirably 150 to 200 parts by weight, and most desirably about 200 parts by weight, based on 100 parts by weight of the paste resin, of a plasticizer. Any of the examples of plasticizer mentioned above may be used for this addition. If the amount of the plasticizer to be added per 100 parts by weight of the paste resin is less than 50 parts by weight, then the adhesive agent to be used in the form of a solution does not exhibit suitable viscosity. If the amount exceeds 350 parts by weight, the solution of the adhesive agent fails to provide ample adhesive strength.

The combination of the vinyl chloride polymer paste resin and the plasticizer may optionally incorporate therein a metal soap of such a metal as lead, cadmium, barium, zinc or calcium with such an organic acid as stearic acid, lauric acid, ricinolic acid, naphthenic acid or 2-ethylhexoic acid or an organic tin such as dibutyl tin dilaurate, dibutyl tin dimaleate or dibutyl tin mercaptide as a stabilizer.

Union of the opposed ends of two tubular members a medical instrument made of vinyl chloride polymer by the use of the adhesive agent prepared by combining the vinyl chloride polymer paste resin and the plasticizer is accomplished by inserting one of the opposed ends of the tubular members into the cavity of the other and applying the aforementioned adhesive agent and about the extreme annular edge of the end overlapping the inserted end. Consequently, the adhesive agent seeps through the gap around the inserted end by capillary action. It is desirable in this case that a crevice should be formed near the annular edge to facilitate the application of the adhesive agent. Alternatively, the union may be accomplished by applying the adhesive agent to the ends for union in advance and then inserting one of the ends into the other.

Examples used to the vinyl chloride polymer of form the medical instrument include a homopolymer of vinyl chloride and copolymers of vinyl chloride with such commonomers as vinylidene chloride, vinyl acatate, vinyl alcohol, ethylene and vinyl bromide. In the case of such a copolymer, the amount of the comonomer to be copolymerized with vinyl chloride is not more than 50 mol%, preferably not more than 30 mol%, most preferably from 3 to 7 mol%.

Now, one preferred embodiment of this invention will be described below with reference to the accompanying drawing. FIG. 1 represents a blood bag in which a blood collection bag 3 which is made of soft polyvinyl chloride and provided with a discharge outlet 1 fitted with a plurality of peel tabs 1(a) and a connecting outlet 2 has its periphery 4 tightly sealed by high-frequency heating and also has connected thereto a blood collection tube 6 made of soft polyvinyl chloride and communicating with the inner cavity 5 of the blood collecting bag. The blood collection bag 3 contains, for example in the inner cavity 5 thereof an ACD-A solution (containing 2.20 g of sodium citrate, 0.80 g of citric acid and 2.20 g of grape sugar in 100 ml of aqueous solution thereof) or a CPD solution (containing 0.327 mg of citric acid, 2.63 g of sodium citrate, 0.251 g of monosodium phosphate and 2.32 g of glucose in 100 ml of an aqueous solution thereof) as an anticoagulant. The aforementioned blood collection tube 6 is provided at the tip thereof with a blood collection needle 7 via hub 23. A cap 8 is fitted on this blood collection needle 7 when the blood bag is not in use.

The blood bag may have at least one other auxiliary bag connected thereto in addition to the aforementioned blood collection bag 3. A first auxiliary bag 13 which is made of soft polyvinyl chloride and provided with discharge outlets 9 each fitted with a peel tab 9(a) and which has its periphery 10 similarly tightly sealed by high-frequency heating and has connected thereto a connection tube 12 made of soft polyvinyl chloride and communicating with an inner cavity 11 is connected via a manifold 14 to a connection tube 16 which is connected to the connecting outlet 2 of the blood collection bag 3 through the medium of a connection needle 15 provided at the leading end of the connection tube 16. A second auxiliary bag 22 which is provided with discharge outlets 17 each fitted with a peel tab 17a and which has its periphery 18 similarly sealed and has connected thereto a connection tube 21 of made soft polyvinyl chloride and communicating with an inner cavity 19 thereof is connected through the medium of the connection tube 21 of its own to the connection tubes 12, 16 via the manifold 14.

Union between tubular members made of vinyl chloride polymer as between the manifold 14 and the connection tubes 12, 16 and 21 or between the connection tube 6 and the hub 23 is accomplished by the use of the aforementioned adhesive agent. Referring to FIG. 2, the union between the blood collection tube 6 and the hub 23, for example, is accomplished by inserting the blood collection tube 6 made of soft vinyl chloride polymer into the central axial hole of the hub 23 of rigid vinyl chloride polymer. As shown in the drawings the blood collection needle 7 is already inserted in hub 23 from the other side into the central axial hole thereof and fastened therein with an adhesive agent 24 such as of the epoxy type introduced through the entrance of the axial hole and spread in the gap surrounding the inserted needle. Adhesive agent 25 prepared by combining the aforementioned vinyl chloride polymer paste resin and the plasticizer is applied to the entrance of the insertion thereby allowing the adhesive agent 25 to fill the gap surrounding the inserted blood collection tube 6 and solidify there as illustrated in FIG. 2.

FIG. 3 illustrates another form of union between the blood collection tube 6 and the hub 23. In this case, the hub 23 of a similar construction which has had the blood collection needle 7 inserted into the central axial hole thereof and fastened there with the adhesive agent 24 such as of the epoxy type has an insertion hole formed on the other side thereof coaxially with the central axial hole. The blood collection tube 6 is made of soft vinyl chloride polymer and is inserted into the insertion hole and the adhesive agent 25, prepared by combining the aforementioned vinyl chloride polymer paste resin and the plasticizer, is applied to the entrance of the insertion hole so as to fasten the inserted blood collection tube 6 in position within the hub 23.

FIG. 4 illustrates one form of union between the connection tubes 12, 16 and 21 and the manifold 23. Specifically, this union is accomplished by inserting the connection tubes 12, 16 and 21 through the respective open ends into the manifold 14 and thereafter applying the aforementioned adhesive agent 25 to the gaps surrounding the inserted portions of the connection tubes.

Also, in the blood bag, the junction can be adopted for the union of the manifold fitted with a blood return inlet and the connection tube. It is also usable for union of tubular members such as in the transfusion set, the transfusion solution filter set and catheter, and the pump type transfusion set.

The present invention will be described more specifically below with reference to the following examples.

EXAMPLE 1

Connection tubes 12, 16, 21 made of soft polyvinyl chloride (combination of 100 parts by weight of polyvinyl chloride having an average degree of polymerization of 1300 and 62 parts by weight of di-2-ethylhexyl phthalate) were inserted into relevant openings of a manifold 14 made of soft polyvinyl chloride (combination of 100 parts by weight of polyvinyl chloride having an average degree of polymerization of 1300 and 40 parts by weight of di-2-ethylhexyl phthalate) as illustrated in FIG. 4. An adhesive agent prepared by combining polyvinyl chloride paste resin having an average degree of polymerization of 1000 and di-2-ethylhexyl phthalate in varying proportions shown in Table 1 was applied to the entrances of the openings. Adhesion of the connection tubes to the manifold was effected in a hot mold kept at 125° C., to complete the junction.

TABLE 1

| Viscosity of adhesive solution | Paste resin (parts by weight) | Di-2-ethylhexyl phthalate (parts by weight) | Temperature for start of gelation (°C.) | Temperature at completion of gelation (°C.) |
| --- | --- | --- | --- | --- |
| ○△* | 100 | 20 | 50 | 125 |
| ○ | 100 | 50 | 52 | 125 |
| ○ | 100 | 70 | 54 | 125 |
| ○ | 100 | 90 | 57 | 125 |
| ◉ | 100 | 110 | 57 | 125 |
| ◉ ◉ | 100 | 150 | 62 | 125 |
| ◉ ◉ | 100 | 200 | 64 | 125 |
| ◉ ◉ | 100 | 250 | 69 | 125 |
| ◉ | 100 | 290 | 70 | 125 |
| ○ | 100 | 350 | 80 | 125 |
| △** | 100 | 400 | 100 | 125 |

In table 1, the viscosity was rated by the four-point scale wherein ◉ ◉ denotes very good viscosity, ◉ fair viscosity, ○ ordinary viscosity and △ bad. * Adhesive agent is too hard after gelation so adhesiveness with the tube is low. ** Viscosity is too low, so gelation is difficult and the hardness after gelation is too low.

EXAMPLE 2

The procedure of Example 1 was followed, except that the adhesive agent was prepared by using as a paste resin a vinyl chloride-vinyl acetate copolymer containing 5 mol% of vinyl acetate. The joined portions were tightened by the use of a hot mold kept at 180° C., or by heating the atmosphere by a far-infrared heater, and the product of the union was treated in an autoclave filled with steam and kept at 120° C. under a gauge pressure (kg/cm²) of 1.5 to 1.7 for 30 minutes. The samples were tested for tensile strength, air tightness and air tightness under pressure before and after the treatment in the autoclave. The results were as shown in Table 2.

The test for tensile strength was carried out by the use of tensile tester, with the joined portions temporarily fastened. The test for air tightness was carried out by first fastening temporarily the joined portions and then exposing the samples to air compressed to 1.0 kg/cm² and noting the presence or absence of air leakage through the joined portions. The test for air tightness under pressure was performed by fastening temporarily the joined portions and exposing the samples to gradually increased air pressure and noting the presence or absence of leakage of compressed air through the joined portions.

TABLE 2

| | Treatment in autoclave | | | | | |
| --- | --- | --- | --- | --- | --- | --- |
| | Before | | | After | | |
| Duration of tightening (seconds) | 5 | 7 | 10 | 5 | 7 | 10 |
| Tensile strength (Kg) | 3.0 | 3.7 | 5.1 | 7.2 | 7.6 | 7.9 |
| Air tightness (leakage) | None | None | None | None | None | None |
| Air tightness under pressure | — | — | — | 4.0 min. | 4.0 min. | 4.0 min. |

From the test results, it is noted that the adhesive agent showed still higher adhesive strength than in the preceding example because it used, as the paste resin, the vinyl chloride-vinyl acetate copolymer containing 5% of vinyl acetate.

As described above, the junction for medical instruments according to the present invention effects union of two tubular members in medical instruments made of polyvinyl chloride by the use of a polyvinyl chloride paste resin incorporating a plasticizer. Unlike the conventional method in which effects the union of tubular members is made by the use of a solvent for polyvinyl chloride, the junction of this invention does not employ such a solvent. Consequently, in the present invention excess solvent will not flow in the gap surrounding the joined portions and find its way into the interior of a medical instrument and thereby contaminate the medicinal solution (e.g. blood) contained within the medical instrument (e.g. blood bag). Since no solvent is used as described above, the tubular members will sustain neither degradation nor cracks and the manufacturing facility will not be contaminated.

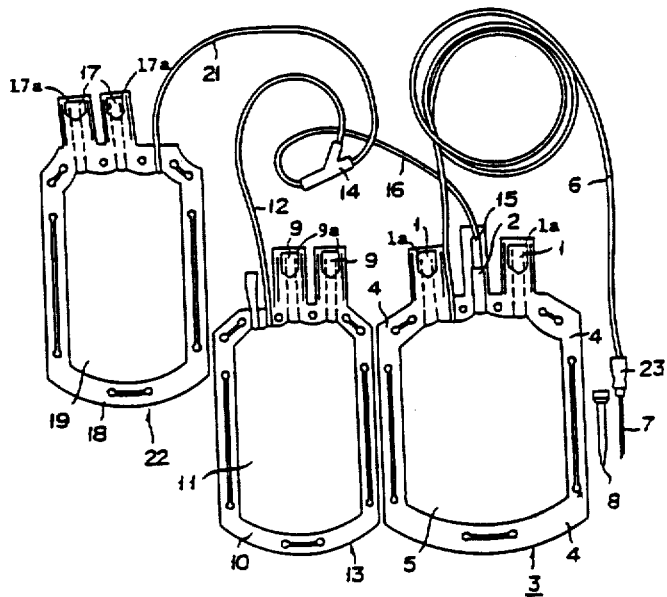

What is claimed is:
1. A method of manufacturing a sterilized medical instrument including at least one pair of tubular members, each of said tubular members being made of a vinyl chloride polymer, said method comprising the steps of:
   insertion of one of said tubular members of said at least one pair of tubular members into the other of said tubular members such that one of said tubular members overlaps the other over a portion of their respective lengths, the overlapping portion forming a junction portion at which said tubular members are to be connected;
   injection of a vinyl chloride resin paste containing from 110 to 290 parts by weight of plasticizer per 100 parts by weight of said vinyl chloride resin between said tubular members along at least a portion of said junction portion to form a joint, said vinyl chloride resin comprising particles having particle diameters between 0.02 and 20 μm;
   first adhesion of said medical instrument including said tubular members with said paste therebetween by heating with the use of a hot mold or heating the atmosphere or a far-infrared heater; and second adhesion of said adhered medical instrument in an autoclave containing pressurized steam to strengthen said joint at about 120° C. under a pressure of 1.5 to 1.7 atmosphere for about 30 minutes.

2. The method of claim 1, wherein said vinyl chloride resin paste is gelled in said joint when it is heated.

3. The method of claim 1, wherein the plasticizer is at least one member selected from the group consisting of phthalic esters, trimellitic esters, aliphatic polybasic acid esters, phosphoric esters, citric esters and butyl phthalyl glycolate.

4. The method of claim 1, wherein the amount of the plasticizer is from 150 to 200 parts by weight per 100 parts by weight of the paste.

5. The method of claim 1, wherein said paste is obtained by dispersing and suspending in the plasticizer, 26 to 48% by weight of said vinyl chloride resin.

6. The method of claim 5, wherein the average degree of polymerization of the vinyl chloride is 900 to 1200.

7. The method of claim 1, wherein the medical instrument is a medical container for holding therein a medicinal solution.

8. The method of claim 7, wherein the container is a blood bag.

9. The method of claim 7, wherein the medical container is a transfusion bag.

10. The method of claim 1, wherein one of said pair of tubular members is a hub and the other of said tubular members is a tube insertable in a hole in said hub.

11. The method of claim 7, wherein one of said tubular members is a tube attached to said medical container and the other of said tubular members is a tube insertable into said tube attached to said medical container.

12. The method of claim 1, wherein one of said tubular members is a manifold having a plurality of openings, the other of said tubular members comprising a plurality of tubes wherein each tube of said plurality of tubes is insertable into one of said openings in said manifold.

13. The method of claim 1, wherein the vinyl chloride resin is a homopolymer of vinyl chloride.

14. The method of claim 1, wherein the vinyl chloride resin of said paste is a copolymer comprising at least 50 mol % of vinyl chloride together with a copolymerizable monomer.

15. The method of claim 14, wherein the copolymerizable monomer is selected from the group consisting of vinylidene chloride, vinyl acetate, vinyl alcohol, and vinyl bromide.

16. The method of claim 15, wherein the copolymerizable comonomer is vinyl acetate.

17. The method of claim 14, wherein the copolymerizable comonomer is present in an amount of up to 30 mol %.

18. The method of claim 15, wherein the copolymerizable monomer is present in an amount of from 3 to 7 mol %.

19. The method of claim 6, wherein the average degree of polymerization of the vinyl chloride resin is 960 to 1130.

20. The method of claim 1, wherein said paste further comprises a stabilizer selected from the group consisting of a metal soap compound and an organic tin compound.

21. The method of claim 16, wherein said vinyl acetate is in an amount of 5%.

22. The sterilized medical instrument manufactured by the method of claim 1.

* * * * *

UNITED STATES PATENT AND TRADEMARK OFFICE
CERTIFICATE OF CORRECTION

PATENT NO. : 4,687,474

DATED : August 18, 1987

INVENTOR(S) : TAKANASHI

It is certified that error appears in the above-identified patent and that said Letters Patent is hereby corrected as shown below:

The title page, showing the illustrative figure, should be deleted and substitute therefor the attached title page.

On the Drawing Sheet, FIG. 1 should be deleted and substitute therefor the FIG. 1 as shown on the attached page.

Column 3, line 40, replace this line with
   --Examples of the vinyl chloride polymer used to form--

Column 5, line 37, Table 1 (in the heading of the fourth
   column), replace "felation" with --gelation--.

Column 6, Table 2, above line 25, after "Air tightness under
   pressure", insert $--kg/cm^2)--$.

Column 7, line 22 (Claim 6), after "vinyl chloride",
   insert --resin--.

UNITED STATES PATENT AND TRADEMARK OFFICE
CERTIFICATE OF CORRECTION

PATENT NO. : 4,687,474

DATED : August 18, 1987

INVENTOR(S) : TAKANASHI

It is certified that error appears in the above-identified patent and that said Letters Patent is hereby corrected as shown below:

Column 8, line 8 (claim 13), after "resin" insert

--of said paste--.

Signed and Sealed this

Twenty-third Day of February, 1993

Attest:

STEPHEN G. KUNIN

*Attesting Officer*    *Acting Commissioner of Patents and Trademarks*

United States Patent [19]

Takanashi

[11] Patent Number: 4,687,474
[45] Date of Patent: Aug. 18, 1987

[54] JUNCTION FOR MEDICAL INSTRUMENTS

[75] Inventor: Nobuyasu Takanashi, Fujinomiya, Japan

[73] Assignee: Terumo Kabushiki Kaisha, Tokyo, Japan

[21] Appl. No.: 815,176

[22] Filed: Dec. 20, 1985

Related U.S. Application Data

[63] Continuation of Ser. No. 742,653, Jun. 10, 1985, abandoned, which is a continuation of Ser. No. 426,204, Sep. 28, 1982, abandoned.

[30] Foreign Application Priority Data

May 28, 1982 [JP] Japan .................................. 57-89863

[51] Int. Cl.$^4$ ............................................ A61M 5/185
[52] U.S. Cl. .................................. 604/257; 604/258; 604/262; 604/409
[58] Field of Search ............... 604/257, 258, 262, 408, 604/411, 6, 86, 414, 415, 403, 905; 285/423, DIG. 10, DIG. 16, DIG. 24, DIG. 20; 156/296, 333

[56] References Cited

U.S. PATENT DOCUMENTS

| | | | |
|---|---|---|---|
| 2,327,128 | 8/1943 | Renfrew et al. | 285/DIG. 24 |
| 2,619,086 | 11/1952 | Wylde | 604/257 |
| 2,949,712 | 8/1960 | Bieberdorf et al. | 604/262 X |
| 4,007,738 | 2/1977 | Yoshino | 604/262 X |
| 4,256,333 | 3/1981 | Jones | 285/423 |
| 4,327,726 | 5/1982 | Kwong et al. | 604/262 |

FOREIGN PATENT DOCUMENTS 715953 9/1954 United Kingdom ............... 156/333

OTHER PUBLICATIONS

Polymer Processing; Schildknecht (editor); vol. X; 1956 Interscience Publishers; New York; pp. 551–557, 563–567.

"Vinyl and Allied Polymers"; vol. 2; Matthews et al.; 1972; ILIFFE Books; pp. 76–83.

Primary Examiner—Richard J. Apley
Assistant Examiner—Alan W. Cannon
Attorney, Agent, or Firm—Frishauf, Holtz, Goodman & Woodward

[57] ABSTRACT

Junction for a medical instrument, which permits the opposed ends for union in two tubular members of a medical instrument made of vinyl chloride polymer to adhere fast to each other with a combination of vinyl chloride polymer paste resin and a plasticizer.

22 Claims, 4 Drawing Figures